(12) United States Patent
Stack et al.

(10) Patent No.: US 6,264,683 B1
(45) Date of Patent: Jul. 24, 2001

(54) STENT DELIVERY CATHETER WITH BUMPERS FOR IMPROVED RETENTION OF BALLOON EXPANDABLE STENTS

(75) Inventors: Richard S. Stack, Chapel Hill, NC (US); Denise Ching, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/527,720

(22) Filed: Mar. 17, 2000

(51) Int. Cl.[7] ........................................... A61F 2/06
(52) U.S. Cl. ............................................... 623/1.11
(58) Field of Search ........................ 606/108, 192, 606/194, 195, 191, 198; 623/1.11

(56) References Cited

U.S. PATENT DOCUMENTS

| | | |
|---|---|---|
| 5,409,495 * | 4/1995 | Osborn .................................. 606/108 |
| 5,810,871 | 9/1998 | Tuckey et al. . |
| 6,068,634 | 5/2000 | Cornelius et al. . |
| 6,106,530 * | 8/2000 | Harada ................................. 606/108 |
| 6,168,617 | 1/2001 | Blaeser et al. . |
| 6,174,316 | 1/2001 | Tuckey et al. . |

* cited by examiner

Primary Examiner—Henry J. Recla
Assistant Examiner—Kevin Truong
(74) Attorney, Agent, or Firm—Fulwider Patton Lee & Utecht, LLP

(57) ABSTRACT

An improved balloon catheter which includes bumpers located adjacent to the proximal and distal ends of the catheter balloon. The bumpers form a recessed pocket into which a stent crimped onto the catheter balloon is mounted. The recessed pocket formed by the bumpers securely retains the stent on the balloon and minimizes undesired contact between the stent and arterial walls and lesions during advancement of the stent within a patient's vasculature.

7 Claims, 2 Drawing Sheets

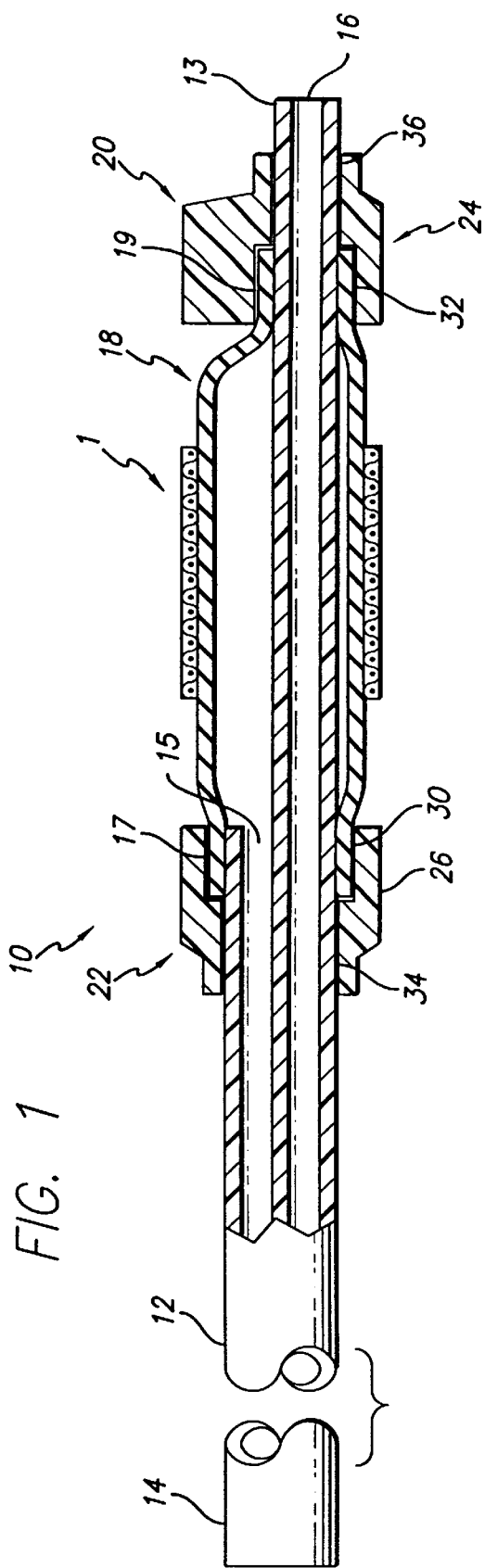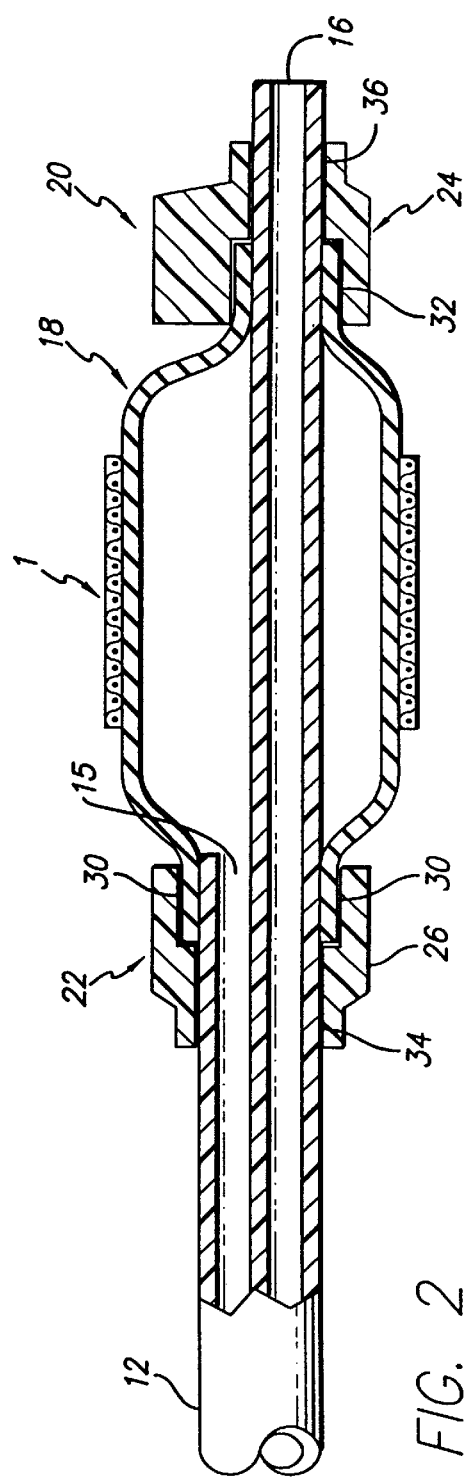

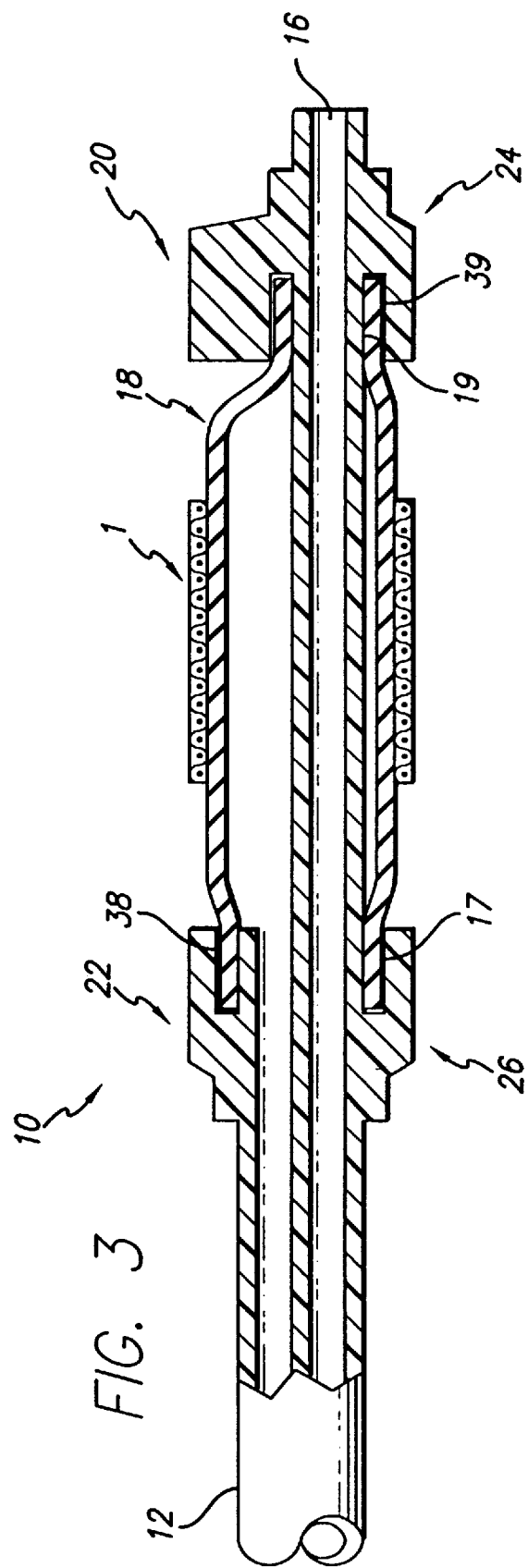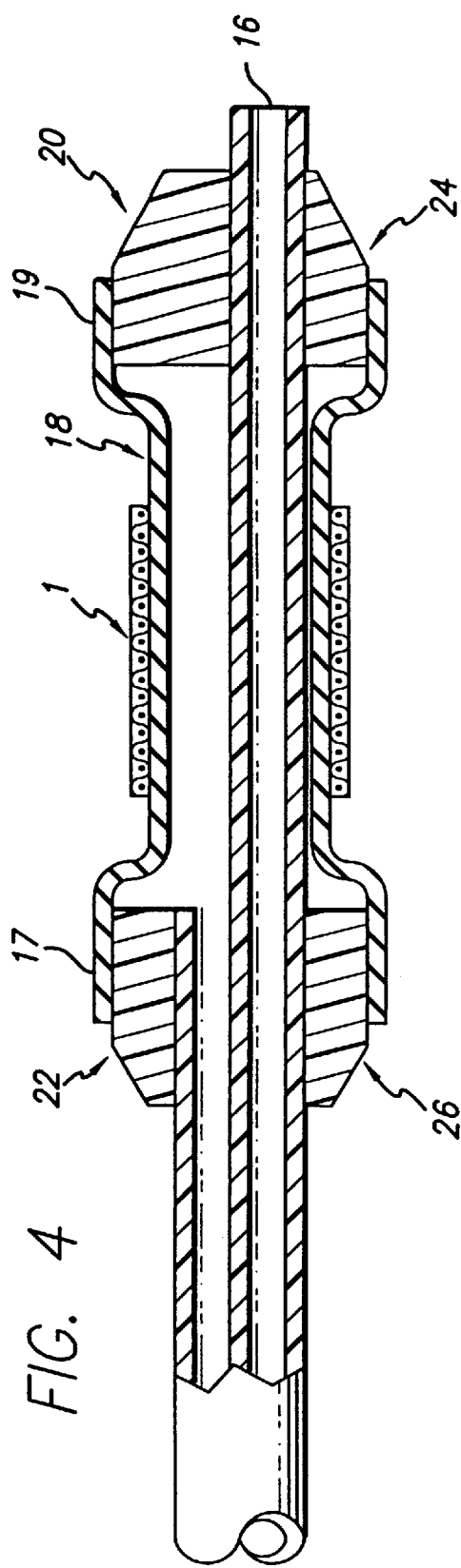

STENT DELIVERY CATHETER WITH BUMPERS FOR IMPROVED RETENTION OF BALLOON EXPANDABLE STENTS

BACKGROUND OF THE INVENTION

The present invention relates to the field of stent delivery systems generally, and more particularly to features for improving stent security on balloon dilatation catheters for use in percutaneous transluminal angioplasty ("PTA") and percutaneous transluminal coronary angioplasty ("PTCA").

In a typical PTCA procedure a guiding catheter having a preformed distal tip is percutaneously introduced through the femoral artery into the cardiovascular system of a patient in a conventional Seldinger technique and advanced within the cardiovascular system until the distal tip of the guiding catheter is seated in the ostium of the desired coronary artery. A guidewire is positioned within an inner lumen of a dilatation catheter and then both are advanced through the guiding catheter to its distal end. The guidewire is first advanced out of the distal end of the guiding catheter into the patient's coronary vasculature until the distal end of the guidewire crosses an arterial lesion. Subsequently, the dilatation catheter having an inflatable balloon on its distal portion is advanced into the patient's coronary anatomy over the previously advanced guidewire until the dilation balloon is properly positioned across the lesion. Once properly positioned the balloon is inflated, with radiopaque liquid at high pressure (about 4–6 atmospheres), to expand the arterial passageway.

In a certain percentage of cases, a dilated arterial wall will collapse upon deflation of the dilation balloon or will slowly narrow over a period of time. To solve this problem, after the initial expansion of the artery, the dilatation catheter is removed and a second dilatation catheter equipped with a stent mounted on the dilation balloon is advanced through the guiding catheter and positioned across the arterial lesion. Once in position the balloon is inflated, expanding the stent and implanting it in the arterial wall. The expanded stent is left in place and supports the interior wall of the artery and thereby prevents arterial collapse or narrowing of the artery over time.

Generally, stents are small tubular metallic structures designed for intravascular placement within an artery. A typical stent-delivery system for balloon expandable stents is characterized by a catheter equipped with a dilation balloon and a stent mounted on the balloon. In such a system, the stent is slipped over a folded catheter balloon and crimped in place. A stent crimped onto a catheter balloon is dependant on friction to hold the stent in position and is therefore subject to slippage while being advanced through the patient's vasculature. Occasionally, during advancement, a stent will slide off of a catheter balloon and migrate within a patient's vasculature necessitating emergency removal procedures. This condition most often occurs in small or heavily occluded arteries where contact with either the arterial wall or the lesion to be treated forces the stent off of the catheter balloon. Additionally, sometimes the stent cannot be deployed for a variety of reasons. In these instances, the stent must be able to be pulled back into the guiding catheter without being "stripped off" of the stent-delivery catheter.

What is needed therefore is a catheter with features that provide for improved stent retention. Such stent retention features should serve to prevent contact between a stent and an arterial wall or lesion and should retain the stent on the catheter balloon if such contact does occur. The present invention satisfies these and other needs.

SUMMARY OF THE INVENTION

The present invention provides an improved balloon catheter for delivery of stents which includes provisions for stent bumpers. The bumpers are located adjacent to the proximal and distal ends of the catheter balloon and form a pocket within which a stent crimped onto the folded balloon is mounted. The bumpers have sufficient height such that the crimped stent does not protrude above the bumpers. Therefore, the stent will remain securely mounted in the pocket formed between the bumpers and cannot slide off the catheter balloon should the stent inadvertently contact the walls of an artery. Additionally, since the crimped stent is recessed within the pocket formed by the bumpers, the likelihood of undesired contact between the stent and an arterial wall or lesion is significantly reduced. In a preferred embodiment, the stent bumpers are formed from a soft pliable material, such as polyamide and polyurethane, in order to minimize the possibility of inflicting trauma upon the walls of the artery during deployment of the stent delivery catheter.

Other features and advantages of the present invention will become more apparent from the following detailed description of the invention, when taken in conjunction with the accompanying exemplary drawings.

BRIEF DESCRIPTION OF THE DRAWINGS

FIG. 1 is a side view, partially in cross section, of a particular embodiment of the improved stent-delivery catheter of the present invention, the catheter being shown in its pre-deployed position;

FIG. 2 is a side view, partially in cross section, of the improved stent-delivery catheter of FIG. 1, the catheter being shown in its deployed position;

FIG. 3 is a side view, partially in cross section, of a particular embodiment of the improved stent-delivery catheter of the present invention, the catheter being shown in its pre-deployed position;

FIG. 4 is a side view, partially in cross section, of a particular embodiment of the improved stent-delivery catheter of the present invention, the catheter being shown in its pre-deployed position.

DETAILED DESCRIPTION OF THE PREFERRED EMBODIMENT

With reference to FIGS. 1 and 2, a preferred embodiment of an improved stent-delivery catheter 10, in accordance with the present invention, is shown. The catheter 10 comprises an elongated catheter shaft 12 having a proximal end (not shown) and a distal end 13, with an inflation lumen 15 and a guidewire lumen 16 extending therebetween. The catheter 10 also includes an expandable member, such as an inflatable balloon 18, mounted on the distal end of the shaft 12, along with a first stent bumper 22 mounted proximally from the inflatable balloon 18, and a second stent bumper 20 mounted distally from the inflatable member 18. The inflatable balloon 18 includes a proximal skirt 17 and a distal skirt 19, which are attached to the catheter shaft 12. FIG. 1 depicts the inflatable balloon 18 of the catheter 10 in its pre-deployed state or collapsed state, with a stent 1 mounted thereon. FIG. 2 depicts the inflatable balloon 18 of the catheter 10 in its expanded state.

The stent bumpers 20 and 22 include openings 34 and 36, which may be in slip fit or interference fit relationship with the catheter shaft 12. The stent bumpers also include intermediate openings 30 and 32 respectively, for receipt of the proximal skirt 17 and distal skirt 19 of the balloon 18. The bumpers 20 and 22 further include cylindrical outside surfaces 26 and 24, which are sized to be larger then the outside diameter of the stent 1, when the stent 1 is crimped onto the catheter balloon. The stent bumpers 22 and 20, thus provide for more secure stent retention on the catheter balloon 18. The bumpers prevent the stent 1 from slipping off the balloon 18 during stent placement within a patient's vasculature and further serve to protect the stent from undesirable contact with arterial walls or lesions, during the placement procedure.

The embodiment of the present invention depicted in FIGS. 1 and 2, wherein the stent bumpers 20 and 22 are discrete components, is advantageous in that the stent bumpers may be made of a material different from the catheter shaft 12. In situations where the risk of trauma to the arterial walls is high, it is desirable to make the stent bumpers 20 and 22 from soft, pliable, polymers which protect the arterial walls from trauma. Suitable materials are polyamide and polyurethane. While these materials possess softness and pliability, they typically do not possess the combination of strength, stiffness, and flexibility required for use in the catheter shaft 12. Therefore, where the risk of trauma to arterial walls is high, the embodiment depicted in FIGS. 1 and 2 may be preferred.

FIG. 3 shows another preferred embodiment of the catheter of the present invention. In this embodiment, the stent bumpers 20 and 22 are integrally formed with the catheter shaft 12, thereby eliminating the need to mechanically secure the bumpers to the shaft. The first and second stent bumpers 22 and 20 include radial grooves 38 and 39 for receipt of the proximal and distal skirts 17 and 19 of the catheter balloon 18. FIG. 3 depicts the catheter balloon 18 in its pre-deployed state with a stent 1 mounted thereon. The primary advantage of the embodiment depicted in FIG. 3 is the simplification in manufacturing that results from forming the stent bumpers 20 and 22 integrally with the catheter shaft 12.

FIG. 4 shows a variation of the embodiment shown in FIG. 3. In FIG. 4, the proximal and distal skirts 17 and 19 of the balloon 18 are fastened to the respective outside diameters 26 and 24 of the stent bumpers 22 and 20. This variation further simplifies manufacturing of the device.

The components of the catheter of the present invention can be formed from a wide variety of conventional materials. The catheter shaft 12 and the stent bumpers 20 and 22 may be made by extruding polymeric materials such as polyethylene, polyvinyl chloride and nylon. Other materials such as polyethylene terephthalate and polyester are also suitable. The stent bumpers also may be made by injection molding techniques. The inflation balloon 18 may be made by blow molding or extruding polymeric materials such as polyamide, polyester, polyolefin, and polyurethane. Other materials and techniques known in the art are also suitable. The balloon 18 and stent bumpers 20 and 22 may be attached to the catheter shaft by any conventional means such as heat welding, solvent welding, ultrasonic welding, or adhesive bonding. Other techniques are also suitable.

The dimensions of the catheter of the present invention generally follow the dimensions of conventional intravascular catheters. For coronary use the catheter shaft 12 is typically about 135 cm in length with a maximum outside diameter of about 0.75 mm to 1.5 mm. Stents for use in coronary applications typically have a crimped diameter of about 1.0 to 1.5 mm. Therefore, the stent bumpers 20 and 22 have a corresponding outside diameter of 1.0 to 1.6 mm. Generally, the preferred stent bumper outside diameter is about 10% greater than that of the stent 1 to be crimped onto balloon 18.

The use of the stent delivery catheter shown in FIGS. 1–4 generally follows conventional PTCA practices with over-the-wire type dilatation catheters. A guidewire (not shown) is backloaded into the guidewire lumen 16 of the catheter shaft 12 and both the guidewire and the stent delivery catheter 10 are advanced together through a guiding catheter (not shown) which has been previously disposed within the patient's arterial system. The distal end of the guiding catheter is seated within the ostium of the artery targeted for treatment, so that, when the delivery catheter-guidewire assembly is advanced through the guiding catheter, the delivery catheter exits directly into the desired artery. The guidewire is usually advanced into the patient's coronary artery until it crosses the lesion to be dilated. Subsequently, the stent-delivery catheter 10 is advanced over the guidewire until the balloon 18 on the catheter 10 is properly disposed within the stenotic region of the patient's artery. Upon proper positioning across the lesion, the balloon is expanded, thus dilating the lesion and implanting the stent 1 within the artery. In some situations, the stenotic region will be pre-dilated before introduction of the stent-delivery catheter 10.

When a prior art stent-delivery catheter is advanced across the stenotic region, stent contact with the lesion typically occurs which creates the possibility of stent slippage on the catheter balloon. If the stent slips proximally, the stent delivery catheter must be withdrawn and a new catheter inserted, thereby prolonging the stent placement procedure which may lead to adverse effects on the patient. If the stents slips distally off of the balloon, the stent may migrate within the patient's vasculature necessitating emergency removal procedures which generally have an adverse effect on the patient. With the catheter of the present invention 10, the stent bumpers 20 and 22 constrain the stent 1 from either proximal or distal slippage, thus eliminating the problem of stent slippage and its associated risks to the patient. Further, the stent bumpers 20 and 22 tend to protect the stent 1 from contact with the lesion which reduces both stent slippage and the undesirable possibility of emboli formation. Emboli are particles of the lesion which may be formed by abrasion with the stent. Embolic particles are undesirable in that they flow freely within the patient's vasculature and may cause blockages in other blood vessels within the patient.

It will be appreciated that an improved stent-delivery catheter has been presented. While only the presently preferred embodiments have been presented in detail, as will be apparent to those skilled in the art, modifications and improvements may be made to the device and method disclosed herein without departing from the scope of the invention. Accordingly, it is not intended that the invention be limited except as by the appended claims.

What is claimed:

1. A catheter for the delivery of a stent comprising:
    an elongated catheter shaft having a proximal end and a distal end, with an inflation lumen extending therebetween;
    a first bumper and a second bumper positioned adjacent to the distal end of the catheter, each bumper being secured to the catheter shaft and having an outer surface; and
    an expandable member attached to the outer surface of the first bumper and second bumper, the expandable member being in fluid communication with the inflation lumen, wherein the area between the first bumper and second bumper form a pocket for receipt of a stent when the expandable member is uninflated.

2. The delivery catheter of claim 1, wherein the bumpers are made from a soft, pliable material.

3. The delivery catheter of claim 1, wherein the bumpers are made from an elastomeric material.

4. The delivery catheter of claim 3, wherein the elastomeric material is polyurethane.

5. The delivery catheter of claim 3, wherein the elastomeric material is polyamide.

6. The delivery catheter of claim 1, wherein the first and second bumpers have an outside diameter which is greater than the outside diameter of a stent crimped over the expandable member.

7. The delivery catheter of claim 1, wherein the expandable member has a sleeve-like shape with a first end and a second end, the first end of the expandable member being attached to the outer surface of the first bumper and the second end of the expandable member being attached to outer surface of the second bumper.

* * * * *